United States Patent
Chen et al.

(10) Patent No.: US 10,227,624 B2
(45) Date of Patent: Mar. 12, 2019

(54) REAGENTS AND KIT COMPOSITIONS FOR SINGLE-CELL WHOLE GENOME AMPLIFICATION

(71) Applicant: Fluidigm Corporation, South San Francisco, CA (US)

(72) Inventors: Peilin Chen, South San Francisco, CA (US); Jing Wang, South San Francisco, CA (US); Andrew May, South San Francisco, CA (US)

(73) Assignee: Fluidigm Corporation, South San Francisco, CA (US)

(*) Notice: Subject to any disclaimer, the term of this patent is extended or adjusted under 35 U.S.C. 154(b) by 463 days.

(21) Appl. No.: 14/800,548

(22) Filed: Jul. 15, 2015

(65) Prior Publication Data
US 2016/0017395 A1    Jan. 21, 2016

Related U.S. Application Data

(60) Provisional application No. 62/026,546, filed on Jul. 18, 2014.

(51) Int. Cl.
| | | |
|---|---|---|
| *C12Q 1/68* | (2018.01) | |
| *C12P 19/34* | (2006.01) | |
| *C12Q 1/6844* | (2018.01) | |
| *C12Q 1/6848* | (2018.01) | |
| *C12Q 1/683* | (2018.01) | |

(52) U.S. Cl.
CPC ............ *C12P 19/34* (2013.01); *C12Q 1/6846* (2013.01); *C12Q 1/6848* (2013.01)

(58) Field of Classification Search
CPC ........ C12Q 2525/113; C12Q 2525/179; C12Q 2527/101; C12Q 2527/125; C12Q 2531/119; C12Q 1/6846; C12Q 1/6848; C12P 19/34
See application file for complete search history.

(56) References Cited

U.S. PATENT DOCUMENTS

| | | |
|---|---|---|
| 6,323,009 B1 | 11/2001 | Lasken et al. |
| 6,617,137 B2 | 9/2003 | Dean et al. |
| 6,977,148 B2 | 12/2005 | Dean et al. |
| 7,047,600 B2 | 7/2006 | Dean et al. |
| 7,205,129 B1 | 4/2007 | Dean et al. |
| 2004/0248105 A1 | 12/2004 | Kumar |
| 2005/0221304 A1 | 10/2005 | Xiang et al. |
| 2012/0171726 A1* | 7/2012 | Eshoo ................ C12P 19/34 435/91.2 |
| 2015/0275282 A1* | 10/2015 | Heller ................ C12P 19/34 435/91.2 |

FOREIGN PATENT DOCUMENTS

| | | |
|---|---|---|
| WO | 02/00934 A2 | 1/2002 |
| WO | 2004/085681 A1 | 10/2004 |
| WO | 2008/151023 A2 | 12/2008 |
| WO | 2012/092433 A1 | 7/2012 |
| WO | 2014/077822 A1 | 5/2014 |

OTHER PUBLICATIONS

Pan, X. et al., A procedure for highly specific, sensitive, and unbiased whole-genome amplification, vol. 105, pp. 15499-15504 (Year: 2008).*
Skerra, A. "Phosphorothioate primers improve the amplification of DNA sequences by DNA polymerases with proofreading activity," Nucleic Acids Research, 1992, vol. 20, No. 14, pp. 3551-3554.
Dean et al.,"Comprehensive human genome amplification using multiple displacement amplification", *Proc Natl Acad Sci USA*, 99:5261-5266 (2002).
Lage et al., "Whole genome analysis of genetic alterations in small DNA samples using hyperbranched strand displacement amplification and array-CGH", *Genome Res.* 13: 294-307 (2003).
Pinard et al., "Assessment of whole genome amplification-induced bias through high-throughput, massively parallel whole genome sequencing", *BMC Genomics* 7:216-236 ( 2006).
Uda et al., "Comparison of Whole Genome Amplification Methods for Detecting Pathogenic Bacterial Genomic DNA Using Microarray", *Jpn J Infect Dis.* 60:355-361 (2007).
Zong et al., "Genome-Wide Detection of Single-Nucleotide and Copy-Number Variations of Single Human Cell", *Science* 338:1622-1626 (2012).
International Search Report and Written Opinion dated Oct. 26, 2015 for PCT Patent Application No. PCT/US2015/040611, 17 pages.

* cited by examiner

*Primary Examiner* — Teresa E Strzelecka
(74) *Attorney, Agent, or Firm* — Kilpatrick Townsend & Stockton LLP (57) ABSTRACT

The present invention provides reagents, kits, and methods for single-cell whole genome amplification using Phi 29 DNA polymerase.

21 Claims, 4 Drawing Sheets
Specification includes a Sequence Listing.

FIG. 1

| pN6_NA1 | /5Phos/ C(N:25252525)(N) (N)*(N)*(N)* N |
| pN6_NA2 | /5Phos/A C(N:25252525)(N) (N).(N)*(N)* N |
| pN6_NA3 | /5Phos/CA C(N:25252525)(N) (N)*(N)*(N)* N |
| pN6_NA4 | /5Phos/ACA C(N:25252525)(N) (N)*(N)*(N)* N |
| pN6_NA5 | /5Phos/G ACA C(N:25252525)(N) (N)*(N)*(N)* N |
| pN6_NA6 | /5Phos/TG ACA C(N:25252525)(N) (N)*(N)*(N)* N |
| pN6_NA7 | /5Phos/ CTG ACA C(N:25252525)(N) (N)*(N)*(N)* N |
| pN6_NA8 | /5Phos/A CTG ACA C(N:25252525)(N) (N)*(N)*(N)* N |
| pN6_NA9 | /5Phos/GA CTG ACA C(N:25252525)(N) (N)*(N)*(N)* N |
| pN6_NA10 | /5Phos/AGA CTG ACA C(N:25252525)(N) (N)*(N)*(N)* N |

REAGENTS AND KIT COMPOSITIONS FOR SINGLE-CELL WHOLE GENOME AMPLIFICATION

REFERENCE TO SUBMISSION OF A SEQUENCE LISTING

This application includes a Sequence Listing as a text file named 085665-0950663_SEQ_ST25.txt created Sep. 22, 2015, and containing 4,121 bytes. The material contained in this text file is incorporated by reference in its entirety for all purposes.

BACKGROUND OF THE INVENTION

Whole genome amplification (WGA) can be performed using three types of chemistry: Primer Extension Preamplification PCR (PEP-PCR), degenerate oligonucleotide primer PCR (DOP-PCR), and multiple displacement amplification (MDA). MDA, particularly Phi 29 DNA polymerase based MDA, is the method most frequently employed, and is a less biased amplification method for WGA (Dean et al., *Proc Natl Acad Sci USA* 99:5261-5266, 2002; Pinard et al., *BMC Genomics* 7:216-236, 2006; Uda et al., *Jpn J Infect Dis.* 60:355-361, 2007). However, existing methods using Phi 29 can have a higher allelic dropout rate and less sensitivity for some applications where the amount of genomic DNA in the reaction is limited. Further, it has been suggested that Phi 29 DNA polymerase-based WGA can exhibit unbalanced or uneven amplification across the genome due to the nature of the enzyme (Zong et al., *Science* 338:1622-1626, 2012; Lage et al., *Genome Res.* 13: 294-307, 2003). An improved method for single-cell WGA is thus needed to facilitate single-cell genome research.

BRIEF SUMMARY OF THE INVENTION

The present invention, is based, in part on the discovery of a design for primers and reaction buffer to improve WGA sensitivity using MDA where only small quantities of DNA, e.g., from a single cell, are analyzed. MDA involves the binding of random hexamers to denatured DNA followed by strand displacement synthesis at a constant temperature using the Phi29 polymerase. Additional priming events can occur on each displaced strand leading to a network of branched DNA structures. The present invention provides improved primers and buffer conditions that are useful for reactions amplifying small initial quantities of nucleic acids, typically genomic DNA from a single cell, to achieve uniform amplification across the genome.

In one aspect, the invention provides a method of amplifying small quantities of genomic DNA, e.g., from a single cell, the method preparing a reaction mixture comprising (i) genomic DNA from a single cell; (ii) random primers comprising from 5' to 3': an NA region, an N region, and an *N region, wherein the primers have the sequence $NA_{1-10}N_{3-5}(*N)_{1-3}$, wherein $NA_{1-10}$ is a defined sequence of from 1-10 nucleotides in length, $N_{3-5}$ is a region of 3-5 nucleotides in length at which random nucleotides are incorporated at each position, and $(*N)_{1-3}$ is a region from 1 to 3 nucleotides in length wherein the nucleotide at each position is a thiolated random nucleotide that provides a phosphorothioate linkage; (iii) a Phi29 DNA polymerase and dNTPs; (iv) buffering agent to provide a pH of about 7.0 to about 7.7, e.g., Tris-HCl at a concentration in the range of about 5 mM to about 50 mM Tris-HCl; (b) incubating the reaction mixture at a temperature in the range of about 30° C. to about 40° C. for a time sufficient to obtain an amplified product. In some embodiment, $NA_{1-10}$ is 4 to 10 nucleotides in length. In some embodiments, $NA_{1-10}$ is 7 to 10 nucleotides in length. In some embodiments, the 3' nucleotide of $NA_{1-10}$ is G or C. In some embodiments, the $NA_{1-10}$ region is 4 to 10 nucleotides in length wherein purine nucleotides are alternated with pyrimidine nucleotides. In some embodiments, $N_{3-5}$ is three nucleotides in length and $(*N)_{1-3}$ is three nucleotides in length. In some embodiments, the reaction is performed at a temperature ranging from about 35° C. to about 40° C. In some embodiments, the reaction is performed at a temperature ranging from about 37° C. to about 40° C. In some embodiments, Tris-HCl is at a concentration in the range of about 10 mM to about 30 mM. In some embodiments, the pH of the reaction mixture is about 7.5. The reaction mixture may further comprise additional components, e.g., DTT at a concentration in the range of 1 to 5 mM and/or $(NH_4)_2SO_4$ at a concentration of 10 mM.

In a further aspect, the invention provides a reaction mixture for amplification of small quantities of DNA, e.g., genomic DNA from a single cell, comprising: (i) random primers comprising from 5' to 3': an NA region, an N region, and an *N region, wherein the primers have the sequence $NA_{1-10}N_{3-5}(*N)_{1-3}$, wherein $NA_{1-10}$ is a defined sequence of 1-10 nucleotides in length, $N_{3-5}$ is a region of 3-5 nucleotides in length at which random nucleotides are incorporated at each position, and $(*N)_{1-3}$ is a region of 1 to 3 nucleotides in length wherein the nucleotide at each position is a thiolated random nucleotide that provides a phosphorothioate linkage; (ii) a Phi29 DNA polymerase and dNTPs; (iii) a buffering agent to provide a pH of about 7.0 to about 7.7, e.g., Tris-HCl at a concentration of about 5 mM to about 50 mM Tris-HCl. In some embodiments, the $NA_{1-10}$ region is 4 to 10 nucleotides in length. In some embodiments, the $NA_{1-10}$ region is 7 to 10 nucleotides in length. In some embodiments, the 3' nucleotide of $NA_{1-10}$ is G or C. In some embodiments, the $NA_{1-10}$ region is 4 to 10 nucleotides in length wherein purine nucleotides are alternated with pyrimidine nucleotides. In some embodiments, $N_{3-5}$ is three nucleotides in length and $(*N)_{1-3}$ is three nucleotides in length. In some embodiments, Tris-HCl is at a concentration of about 10 mM to about 30 mM. In some embodiments, the pH of the reaction mixture is about 7.5. The reaction mixture may further comprise additional reagents, e.g., DTT at a concentration of 1 to 5 mM and/or $(NH_4)_2SO_4$ at a concentration of 10 mM.

In a further aspect, the invention provides random primers comprising from 5' to 3': an NA region, an N region, and an *N region, wherein the primers have the sequence $NA_{1-10}N_{3-5}(*N)_{1-3}$, wherein $NA_{1-10}$ is a defined sequence of 1-10 nucleotides in length, $N_{3-5}$ is a region of 3-5 nucleotides in length at which random nucleotides are incorporated at each position, and $(*N)_{1-3}$ is a region of 1 to 3 nucleotides in length wherein the nucleotide at each position is a thiolated random nucleotide that provides a phosphorothioate linkage. In some embodiments, the $NA_{1-10}$ region is 4 to 10 nucleotides in length wherein purine nucleotides are alternated with pyrimidine nucleotides. The invention additionally provides kits comprising such primers, optionally wherein the kit further comprises a container that contains a buffer having a pH of about 7.5 that contains from about 5 mM to about 30 mM Tris-HCl. In some embodiments, the kit further comprises 1 to 5 mM DTT and/or 10 mM $(NH_4)_2SO_4$.

In another aspect, the invention provides a method of producing an amplified product, the method comprising: (a) preparing a reaction mixture comprising: (i) genomic DNA from a single cell; (ii) random primers of 40 nucleotides or fewer in length, comprising from 5' to 3': a tag region of at least from 1 to 20 nucleotides in length having a defined sequence, and a random region of from 6 to 20 nucleotides in length at which random nucleotides are incorporated at each position, wherein at least the 3'-end nucleotide of the primer has a phosphorothioate linkage; (iii) a Phi29 DNA polymerase; (iv) a buffering agent to provide a pH of from about 7.2 to about 7.7; and (b) incubating the reaction mixture at a temperature in the range from about 35° C. to about 40° C. for a time sufficient to produce an amplified product.

In another aspect, the invention provides a reaction mixture for amplification of genomic DNA from a single cell comprising: (i) genomic DNA from a single cell; (ii) random primers of 40 nucleotides or fewer in length, comprising from 5' to 3': a tag region of at least from 1 to 20 nucleotides in length having a defined sequence, and a random region of from 6 to 20 nucleotides in length at which random nucleotides are incorporated at each position, wherein at least the 3'-end nucleotide of the primer has a phosphorothioate linkage; (iii) a Phi29 DNA polymerase; and (iv) a buffering agent to provide a pH of from about 7.2 to about 7.7.

BRIEF DESCRIPTION OF THE DRAWINGS

FIG. 2 provides results showing the effects of tag length of 5' phosphorylated primers in accordance with the invention and temperature on the positive rate in a qPCR of WGA products (SEQ ID NOS: 1-7 (pN6_NA4 to pN6_NA10, respectively). The WGA reactions were performed at 30° C. and 40° C. for 3.5 hours using 1.5 µl of denatured genomic DNA at 8 ng/µl and 18.5 µl of a pre-sample mixture. The WGA reaction mixture contains 12 ng genomic DNA, 1X GenomiPhi™ V2 Phi29 enzyme mix, 50 µM of Primer (N6_NA1), 1 mM dNTPs, 10 mM $MgCl_2$, 10 mM $(NH_4)SO_4$ and 50 mM KCl in 37 mM Tris-HCL buffer, pH 7.5. The resulting WGA products were pre-amplified and then quantitated by quantitative PCR (qPCR) on a 96.96 Dynamic Array™ Integrated Fluidic Circuit (IFC) in a BioMark™ system using 96 primers across 22 chromosomes. The positive rate across 96 assays was calculated for those assays with a $C_t$<27. The pre-amplification was carried out by mixing 1.25 ul of the WGA product with 3.75 ul of pre-sample mix. The pre-sample mix consists of 1X Qiagen multiplex PCR master mix (PN 206143), and 96 target primers at 50 nM each. The pre-amplification was performed at 95° C. for 15 minutes, followed by 14 cycles of 95° C. for 15 seconds and 60° C. for 4 minutes. The pre-amplified products were diluted by 20 folds with DNA suspension buffer for qPCR on the 96.96 Dynamic Array™ IFC.

DETAILED DESCRIPTION OF THE INVENTION

As used herein, the term "whole genome amplification" or "WGA" refers to amplification of an entire genome using small amounts of nucleic acid, e.g., DNA, obtained from a single cell. WGA does not require that 100% of a genome be amplified, but that amplification occurs across a substantial portion of the genome. In some embodiments, greater than 50% of a genome is amplified. In typical embodiments, at least 60%, 65%, 70%, 75%, 80%, 85%, 90%, 95%, or greater of the genomic nucleic acid in a sample is amplified. The present invention employs MDA for single-cell amplification reactions. Accordingly, in the context of the present invention, "WGA" refers to whole genome amplification performed using MDA.

Primer Design

Primers suitable for WGA are sufficiently long to prime the synthesis of extension products in the presence of the agent for polymerization. Conventional MDA uses random hexamers as primers. In the current invention, the primers include both random regions and "tag" regions of defined sequence where the order of the regions is 5' to 3': tag region-random region. A "tag" region as used herein refers to a constant region having a defined sequence. The defined sequence is not selected based on homology to a known sequence, but is designed to have a balance of purine and pyrimidine bases, i.e., the number of pyrimidine nucleotides, e.g., C and T nucleotides, is about equivalent, e.g., equal to or differing by no more than one or two, to the number of purine nucleotides, e.g., G and A nucleotides. In some embodiments, the sequence comprises alternating pyrimidine and purine nucleotides. Preferably, the defined sequence has a G or C immediately preceding the first random nucleotide at the 5' end of the random nucleotide sequence.

The random regions of the primers are generally 6 to 8 or 9 nucleotides in length, but may be anywhere from 6 to 20 nucleotide in length, or even longer. The tag sequence is typically of 1 to 10 nucleotides in length, but may be longer, e.g., up to 15 nucleotides or 20 nucleotides in length. In some embodiments, the tag region of the primer is from 4 to 15 nucleotides in length, i.e., 4, 5, 6, 7, 8, 9, 10, 11, 12, 13, 14, or 15 nucleotides in length. In some embodiment, the tag region of the primer is from 4 to 10 nucleotides in length, i.e., 4, 5, 6, 7, 8, 9, or 10 nucleotides in length. In some embodiments, the tag region of the primer is from 7 to 10 nucleotides in length, i.e., 7, 8, 9, or 10 nucleotides in length. Accordingly, the primers often may range in size from 7 to 40 nucleotides in length. In some embodiments, the primers are from 7 to 18 nucleotides in length. In some embodiments, the primers are at least 13 nucleotides in length, wherein the random region comprises at least 6 nucleotides in length. In a primer of the current invention, the nucleotide at the 3'-end of the primer, which is in the random region, has an exonuclease-resistant linkages, e.g., 2-phophorothioate and 1-phosphorodithioate linkage. In typical embodiments, the nucleotide at the 3' end of the primer has a phosphorothioate linkage. In some embodiments, two or three, or more, of the nucleotides at the 3' end of the primers have exonuclease-resistant linkages, e.g., phosphorothioate linkages.

As understood by one of skill in the art in this field, "a primer" or "a random primer" for use in WGA refers to a pool of primers which may be generated by randomizing a nucleotide at any given location in an oligonucleotide sequence in such a way that the given location may have all of the possible nucleotides present at that location. The pool resulting from the randomization has many, essentially all, of the different random sequences present. Methods of randomization are well known in the art.

In some embodiments, primers in accordance with the invention for use in WGA for small quantities of nucleic acids, e.g., single-cell WGA, are phosphorylated at the 5' end and are designed based on the following general formula (5' to 3'): $NA_{1-10}N_{3-5}(*N)_{1-3}$, where NA is a tag region representing a constant region having a defined sequence; N represents a random nucleotide, and *N represents a modified random nucleotide that is resistant to nucleases, for example a phosphorothioate nucleotide.

As explained above, the defined nucleic acid sequence ($NA_{1-10}$) is not selected based on homology to a known sequence, but is designed to have a balance of purine and pyrimidine bases, i.e., the number of pyrimidine nucleotides, e.g., C and T nucleotides, is about equivalent, e.g., equal to or differing by no more than one, to the number of purine nucleotides, e.g., G and A nucleotides. In some embodiments, the sequence comprises alternating pyrimidine and purine nucleotides. Preferably, the defined sequence has a G or C immediately preceding the first random nucleotide at the 5' end of the random nucleotide sequence. In some embodiment, this region of the primer is from 4 to 10 nucleotides in length, i.e., 4, 5, 6, 7, 8, 9, or 10 nucleotides in length. In some embodiments, this region of the primer is from 7 to 10 nucleotides in length, i.e., 7, 8, 9, or 10 nucleotides in length.

The primer region that comprises random nucleotides is generated such that the collection of primers used for single-cell WGA has a random nucleotide at each of the positions in the random region, e.g., in the $N_{3-5}$ region of the primer design formula. Accordingly, every, or essentially every, possible nucleotide sequence for a random region, e.g., the $N_{3-5}$ region, is represented in the set of primers. Use of random primers for MDA reactions is described, e.g., in U.S. Pat. No. 6,977,148. In the formula explained above, the $(*N)_{1-3}$ region also comprises from 1 to 3 random nucleotides; however, the nucleotides are modified to be resistant to nucleases. Typically, the modified nucleotide is a thiolated nucleotide that provides a phosphorothioate linkage. In some embodiments, the modified nucleotide is another exonuclease-resistant nucleotide such as that described below. In some embodiments, the $(*N)_{1-3}$ region may have a mixture of exonuclease-resistant linkages, e.g., 2-phophorothiote and 1-phosphorodithioate linkages. In some embodiments, the $(*N)_{1-3}$ region has one or more phosphorothioate bonds, which are resistant to most exonucleases (Putney et al., Proc. Natl. Acad. Sci. USA 78:7350-7354, 1981; Skerra, Nucleic Acids Res. 20:3551-3554, 1992). In some embodiments, the "N" region and "*N" region together provide a random sequence of from 6 to 8 nucleotides in length. Thus, in some embodiments, primers of the invention have random regions of 6 to 8 nucleotides in length with from 1 to 3 phosphorothioate bonds at the 3' end.

A primer of the invention may also comprise other modified nucleotides. Many modified nucleotides are known. A modification may be to either to the base, sugar, or phosphate moieties, or to one or more of these moieties. In some embodiments, modifications to the sugar linkage of the primers (including but not limited to 2' O-methyl, 2' O-fluoro) may also be employed. Examples of modified bases include but are not limited to 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Other modified bases are those that are universal bases, which do not have bias in base pairing. Universal bases include 3-nitropyrrole and 5-nitroindole.

Modified nucleotides can also include modifications of the sugar moiety. Such modifications include natural modifications of as well as synthetic modifications. Sugar modifications include but are not limited to the following modifications at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10, alkyl or C2 to C10 alkenyl and alkynyl. Nucleotide sugar analogs may also have sugar mimetics such as cyclobutyl moieties in place of the pentofuranosyl sugar. Many modifications are known. Examples of patents that teach such modified sugars include U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference.

As noted above, modified nucleotides include those that are modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkages between two nucleotides can be through a 3'-5' linkage or a 2'-5' linkage, and the linkage can contain inverted polarity such as 3'-5' to 5'-3' or 2'-5' to 5'-2'. Numerous United States patents teach how to make and use nucleotides containing modified phosphates and include but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Primers of the invention are used to randomly prime the target genomic nucleic acid for amplification. In the present invention, "randomly prime" refers to hybridizing to multiple sites within template polynucleotide that are not predetermined and provides for substantially unbiased WGA.

Primers having the formula described herein are used in amplification reactions performed on a small quantity of nucleic acids, typically genomic DNA from a single cell.

The primers provide uniform amplification across the genome at a higher temperature, e.g., from about 37° C. to about 40° C., than the 30° C. temperature employed in standard MDA reactions. Assays to determine uniformity of amplification are known in the art. Such assays include comparative genomic hybridization and analysis of a panel of SNPs selected to cover the desired set of chromosomes. An illustrative assay to evaluate uniform amplification is as follows. Genomic DNA (e.g., from about 6 to about 1,000 pg) is amplified in a reaction mixture containing 37 mM Tris-HCl, pH 7.5; 10 mM $MgCl_2$, 10 mM $(NH_4)_2SO_4$, and 50 mM KCl using primers designed in accordance with the invention. The reaction is performed at 38° C. for 2-3 hours. Amplified products are then evaluated to determine uniform amplification, e.g., using pre-amplification and qPCR on an IFC designed to detect amplification across the desired set of chromosomes. Primers that are suitable for use for WGA provide a low allelic dropout-rate when analyzing alleles across the genome. WGA performed using such primers detects at least 85% of the alleles, preferably at least 90% or at least 95%, or more, of the alleles in the SNP analysis. For example, a panel of 96 SNPs in the Fluidigm 96.96 Dynamic Array™ is used to measure the allelic drop-out rate for assessing primer performance in WGA across 22 chromosomes. Primers designed in accordance with the invention that can detect at least 85% of the alleles, preferably at least 90%, or at least 95% of the alleles in the assay, are suitable for WGA of small quantities of nucleic acids, e.g., single-cell WGA.

Whole Genome Amplification Reaction Components.

The present invention employs MDA for amplification reactions using small quantities of nucleic acid, e.g., single-cell amplification reactions. MDA is a non-PCR-based isothermal method based on the annealing of random primers to denatured DNA, followed by strand-displacement synthesis at constant temperature. It has been applied to small genomic DNA samples, leading to the synthesis of high molecular weight DNA with limited sequence representation bias. As DNA is synthesized by strand displacement, a gradually increasing number of priming events occur, forming a network of hyper-branched DNA structures.

A reaction in accordance with the invention employs a strand displacing nucleic acid polymerase. Such a polymerase has strand displacement activity apart from its nucleic acid synthesis activity. Typically, MDA is performed using a Phi29 DNA polymerase, which has strand displacement activity and proofreading activity resulting in error rates 100 times lower that than of Taq polymerase. In other embodiments, the large fragment of a Bst DNA polymerase may be employed.

Suitable reaction mixtures for performing WGA using small amounts of nucleic acids, e.g., from a single cell, include a buffering agent such as Tris, magnesium ions, nucleotides, optionally salts, such as sodium or potassium chloride, ammonium sulfate, and the like. An exemplary reaction mixture for WGA contains a source of magnesium ions, e.g., $MgCl_2$, at a concentration of about 1 to about 10 mM, typically 10 mM $MgCl_2$. A reaction mixture for use in the invention also employs a buffering agent, typically Tris, at a concentration of about 5 to about 75 mM, or of about 5 to about 50 mM, typically about 10 to about 30 mM. Optionally, the buffer may contains salt, e.g., KCl, typically at a concentration of about 1 to about 100 mM, e.g., about 50 mM. The reaction mixture may optionally comprise additional reagents such as a stabilizing agent, e.g., DTT, Cleland's reagent or mercaptoethanol. The stabilization agent is typically included in a concentration of about 10 mM or below, e.g., about 1 to about 5 mM. In typical embodiments, the reaction mixture also comprises ammonium sulfate, e.g., at a concentration of about 1 to about 20 mM, e.g., 10 mM, to further enhance the reaction. The reaction mixture also comprises dNTPs. Concentrations of dNTPs suitable for use are known in the Art. For example, the dNTP concentration in the reaction mixture can be in the range of about 10 μM to about 1000 mM, typically in the range of about 100 μM to about 100 mM. Examples of dNTP concentrations are 50 μM, 100 μM, 500 μM, 1 mM, 5 mM, 10 mM and 100 mM. Detergents such as Tween 20, Triton X 100, and Nonidet P40 may also be included in the reaction mixture. The reaction mix can have a pH range of about 7.0 to about 9.0, with a pH range of about 7.3 or about 7.4 to about 8.0 as typical. In some embodiments, the pH is about 7.5.

The concentration of primers employed for the reaction can vary and can be readily determined by one of skill in the art. For example, a primer concentration of anywhere from about 5 μM to about 100 μM can be used. Typically, the primers are at a concentration of about 25 μM to about 70 μM. In some embodiments, the primers are at a concentration of about 40 μM to about 60 μM.

The amount of genomic nucleic acid, e.g., DNA, to be amplified in the WGA reaction is a small amount, typically the amount present in a single cell. In some embodiments, genomic DNA in an amount of about 0.5 pg to about 1000 pg, or about 1 pg to about 100 pg, or about 1 pg to about 10 pg, is used for the WGA reaction. In some embodiments, a larger amount of genomic DNA can be amplified in a WGA using a primer of the invention. For example, in some embodiments, 10 ng or less of genomic DNA may be employed in the reaction.

A WGA reaction using a primer in accordance with the invention can be performed at a higher reaction temperature than standard WGA reactions. Higher reaction temperatures permit shorter incubation times and provide more even amplification. Thus, although a WGA reaction using a primer of the invention can be performed at about 30° C., the reaction is often carried out at a temperature ranging from about 32° C. to about 40° C., typically from about 35° C. to about 40° C. In some embodiments, the reaction is performed at about 37° C. to about 40° C. In some embodiments, the reaction is performed at about 35° C., about 36° C., about 37° C., about 38° C., about 39° C., or about 40° C.

The reaction volume is typically a volume suitable for WGA using small quantities of DNA, such as single-cell WGA. In some embodiments, e.g., where the reaction vessel is chamber or a channel of a microfluidic device, the volume is the range of about 0.2 nL to about 200 nL. In some embodiments, the reaction volume is in the range of about 1 nL to about 100 nL, or in the range of about 0.5 nL to about 50 nL. In some embodiments, the volume is in the range of about 1 nL to about 20 nL or about 1 to about 15 nL. In some embodiments, the incubation volume is less than any one of the following amounts: about 200 nL, about 100 nL, about 50 nL, about 25 nL, about 10 nL, about 5 nL, or about 1 nL.

In some embodiments, a WGA in accordance with the invention may be performed in a droplet. The volume of droplet is typically on the order of picoliters to nanoliters. Multiple droplets can be fused to bring reaction reagents into contact. In some embodiments, a sample droplet may contain genomic DNA from a single cell. In some embodiments, a droplet containing the genomic nucleic acid for amplification may be combined with a droplet containing reagents for the WGA reaction. In some embodiments, for example, where a WGA reaction is performed in a microfluidics device, the droplet has a diameter that is smaller than the diameter of the microchannel, e.g., less than 60 microns or less than 30 microns. Droplet dimensions and flow characteristics can be influenced as desired, in part by changing the channel dimensions, e.g. the channel width. In some embodiments, the droplets of aqueous solution have a volume of approximately 0.1 to 100 picoliters (pl). Use of droplets for reactions is known in the art. Descriptions of droplet analysis using a microfluidics device are found, e.g., in U.S. patent application publication no. 20120276544 and Mazutis et al., *Nature Protocols* 8:870-891, 2013, which are incorporated by reference.

The WGA reactions can be carried out for a time period typically ranging from 1 to 4 hours. In some embodiments, the reaction time is less than 3 hours, e.g., 2 hours.

Single Cell Amplification

The WGA reactions described herein are typically conducted on single cells where the genomic DNA from only one cell is amplified in the reaction. In some embodiments, an assay is performed using a small number (e.g., fewer than 100, fewer than 50, fewer than 10, or fewer than 5) of cells. In one approach employing a single cell, the cell is isolated and lysed; and reagents, including primers and other amplification reagents, are added directly to the lysate to perform the assay. In some embodiments, the isolation of single cells and WGA are carried out using a microfluidic device. Microfluidic systems for single-cell analysis applications are known. An exemplary device is the $C_1$™ Single-Cell Auto Prep System which is commercially available from Fluidigm Corp. 7000 Shoreline Court, Suite 100, South San Francisco, Calif.). The $C_1$™ Single-Cell Auto Prep System isolates single cells, lyses them, and carries out a series of reactions from the lysate (e.g., nucleic acid amplification, etc.). Other devices are described in U.S. Pat. Application Publication No. 20130302883, entitled "Methods, Systems, And Devices For Multiple Single-Cell Capturing And Processing Using Microfluidics", which is incorporated by reference in its entirety for all purposes. Optionally the $C_1$™ Single-Cell Auto Prep System may be used in conjunction with Fluidigm's BioMark™ HD System (Fluidigm Corp. 7000 Shoreline Court, Suite 100, South San Francisco, Calif.). U.S. patent application Ser. No. 13/781,292 filed Feb. 28, 2013 is incorporated herein in its entirety all purposes.

Single-cell studies within microfluidic architectures may involve the isolation of individual cells into individual reaction partitions (chambers, droplets, cells). Limiting dilution is one method for achieving this isolation. Cells may be loaded at concentrations of less than one cell per partition on average, and distribute into those partitions in a pattern described by Poisson statistics. Another approach is to rely on mechanical traps to capture cells. These traps are designed to capture cells of a given size range.

Other devices for manipulation of single cells include those described in the following: Sims et al., 2007, "Analysis of single mammalian cells on-chip" Lab Chip 7:423-440; Wheeler et al., 2003, "Microfluidic device for single-cell analysis" Anal Chem 75:3581-3586; Skelley et al., 2009 "Microfluidic control of cell pairing and fusion" Nat Methods 6:147-152; Marcus et al., 2006, "Microfluidic single-cell mRNA isolation and analysis" Anal Chem 78:3084-3089; Bontoux et al., 2008 "Integrating whole transcriptome assays on a lab-on-a-chip for single-cell gene profiling" Lab Chip 8:443-450; Zhong et al., 2008 "A microfluidic processor for gene expression profiling of single human embryonic stem cells" Lab Chip 8:68-74; Wheeler 2003 "Microfluidic Device for Single-Cell Analysis Anal. Chem." 75:3581-3586; and White et al., Aug. 23, 2011 "High-throughput microfluidic single-cell RT-qPCR PNAS" Vol. 108, 34:13999-14004; each of the aforelisted publications is incorporated herein by reference.

Cells for single-cell analysis can be obtained from eukaryotic or prokaryotic organisms. Eukaryotics cells may be from animals, that is, vertebrates or invertebrates. Vertebrates may include mammals, that is, primates (such as humans, apes, monkeys, slender lorises, etc.) or nonprimates (such as cows, horses, sheep, pigs, dogs, cats, rabbits, mice, rats, sugar gliders, and/or the like). Nonmammalian vertebrates may include birds, reptiles, fish, (such as trout, salmon, goldfish, zebrafish, etc.), and/or amphibians (such as frogs of the species *Xenopus, Rana,* etc.). Invertebrates may include arthropods (such as arachnids, insects (e.g., *Drosophila*), etc.), mollusks (such as clams, snails, etc.), annelids (such as earthworms, etc.), echinoderms (such as various starfish, among others), coelenterates (such as jellyfish, coral, etc.), porifera (sponges), platyhelminths (tapeworms), nemathelminths (flatworms), etc Eukaryotic cells may be from any suitable plant, such as monocotyledons, dicotyledons, gymnosperms, angiosperms, ferns, mosses, lichens, and/or algae, among others. Exemplary plants may include plant crops (such as rice, corn, wheat, rye, barley, potatoes, etc.), plants used in research (e.g., *Arabadopsis*, loblolly pine, etc.), plants of horticultural values (ornamental palms, roses, etc.), and/or the like.

Eukaryotic cells may be from any suitable fungi, including members of the phyla *Chytridiomycota, Zygomycota, Ascomycota, Basidiomycota, Deuteromycetes,* and/or yeasts. Exemplary fungi may include *Saccharomyces cerevisiae, Schizosaccharomyces pombe, Pichia pastoralis, Neurospora crassa,* mushrooms, puffballs, imperfect fungi, molds, and/or the like.

Eukaryotic cells may be from any suitable protists (protozoans), including amoebae, ciliates, flagellates, coccidia, microsporidia, and/or the like. Exemplary protists may include *Giardia lamblia, Entamoeba. histolytica, Cryptosporidium,* and/or *N. fowleri,* among othe Eukaryotic cells for analysis may also be immortalized and/or transformed by any suitable treatment, including viral infection, nucleic acid transfection, chemical treatment, extended passage and selection, radiation exposure, and/or the like. Such established cells may include various lineages such as neuroblasts, neurons, fibroblasts, myoblasts, myotubes, chondroblasts, chondrocytes, osteoblasts, osteocytes, cardiocytes, smooth muscle cells, epithelial cells, keratinocytes, kidney cells, liver cells, lymphocytes, granulocytes, and/or macrophages, among others. Exemplary established cell lines may include Rat-1, NIH 3T3, HEK 293, COS 1, COS7, CV-1, C2C12, MDCK, PC12, SAOS, HeLa, Schneider cells, Junkat cells, SL2, and/or the like.

Prokaryotic cells that can be analyzed in accordance with the invention include self-replicating, membrane-bounded microorganisms that lack membrane-bound organelles, or nonreplicating descendants thereof. Prokaryotic cells may be from any phyla, including *Aquificae, Bacteroids, Chlorobia, Chrysogenetes, Cyanobacteria, Fibrobacter, Firmicutes, Flavobacteria, Fusobacteria, Proteobacteria, Sphingobacteria, Spirochaetes, Thermomicrobia,* and/or *Xenobacteria,* among others. Such bacteria may be gram-negative, gram-positive, harmful, beneficial, and/or pathogenic. Exemplary prokaryotic cells may include *E. coli, S. typhimurium, B subtilis, S. aureus, C. perfringens, V. parahaemolyticus,* and/or *B. anthracis,* among others.

As understood in the art, the products of a whole genome amplification reaction can be quantified using various methods known in the art. In preferred embodiments, the reaction products for the WGA can be evaluated by qPCR.

WGA reactions of the invention can be used for any application in which it is useful to evaluate small quantities of nucleic acid, e.g., the genome of a single cell. For example, WGA reactions as described herein can be used for diagnostic applications, e.g., for mutation and/or SNP evaluation for genetic analyses. Such applications include somatic cell genetic analyses, such as those performed to evaluate the genome of a tumor cell for cancer diagnosis and prognosis.

Kits

The invention additionally provides kits comprising primers and reagents for use in the invention. A kit generally includes one or more containers holding the reagent(s), e.g., buffer, primers, polymerase, as one or more separate compositions. WGA primers of the invention may be provided in a kit with a buffer as described herein or may be provided separately. The kit may also include reagents such as Phi29 DNA polymerase. The kit can also include other material(s) that may be desirable for WGA, such as additional reagents components, diluent(s), a standard(s), and/or any other material useful in conducting the assay.

Kits according to the invention generally include instructions for carrying out one or more of the methods of the invention. Instructions included in kits of the invention can be affixed to packaging material or can be included as a package insert. While the instructions are typically written or printed materials they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), RF tags, and the like. As used herein, the term "instructions" can include the address of an internet site that provides the instructions.

The following examples are offered to illustrate, but not to limit, the claimed invention.

EXAMPLES

These examples illustrate a whole genome amplification method suitable for use for single-cell WGA.

Genomic DNA was amplified in a reaction containing 4.2 ng/reaction using a GenomiPhi™ V2 WGA kit from GE Healthcare Life Sciences in accordance with the manufacturer's protocol. The resulting products were directly measured by qQCR on a Fluidigm 96.96 Dynamic Array™ IFC using 96 assays designed across 22 chromosomes. The quantities of amplification products obtained in this experiment suggested that it may be desirable to improve the sensitivity to further facilitate single-cell WGA analyses.

To improve WGA sensitivity, primers were designed and reaction buffers reformulated to enhance the stability of Phi 29 DNA polymerase and primer-enzyme complexes.

A reaction buffer containing 37 mM Tris-HCl, pH 7.5; 1 mM dNTPs, 10 mM MgCl$_2$, 10 mM (NH$_4$)$_2$SO$_4$, and 50 mM KCl was prepared. Whole genome amplification methods were evaluated using 5' phosphorylated randomers (N6-N8) with the sequences as follows: phos-[NA]$_{1-10}$, N$_{3-5}$, (*N)$_{1-3}$, where the randomer nucleotides are represented by N$_{3-5}$ and (*N)$_{1-3}$. The asterisk indicates that the nucleotide is thiolated to provide a phosphorothiolated backbone. Accordingly, the primer has from 1-3 phosphorothioate linkages at the 3' end. As noted, the randomer sequence in the primers is from 6 to 8 nucleotides in length. The sequence [NA]$_{1-10}$ is an empirically determined nucleic acid sequence of from 1 to 10 nucleotides in length that is also included in the primers. These sequences are usually designed to have an equal balance of A/T and G/C, with a "C" or "G" as the nucleotide 5' to the first random nucleotide in the sequence.

A WGA amplification was performed using 50 μM of a primer having a sequence pCNNN*N*N*N and the buffer described in the preceding paragraph and compared to a reaction performed with the GenomiPhi™ V2 WGA kit from GE Healthcare Life Sciences. The results showed that the primers/reaction buffer that were designed in accordance with the above parameters provided an increased yield compared to known kit reagents, particularly, when the reaction was performed at 40° C. in comparison to 30° C.

Figure 2:
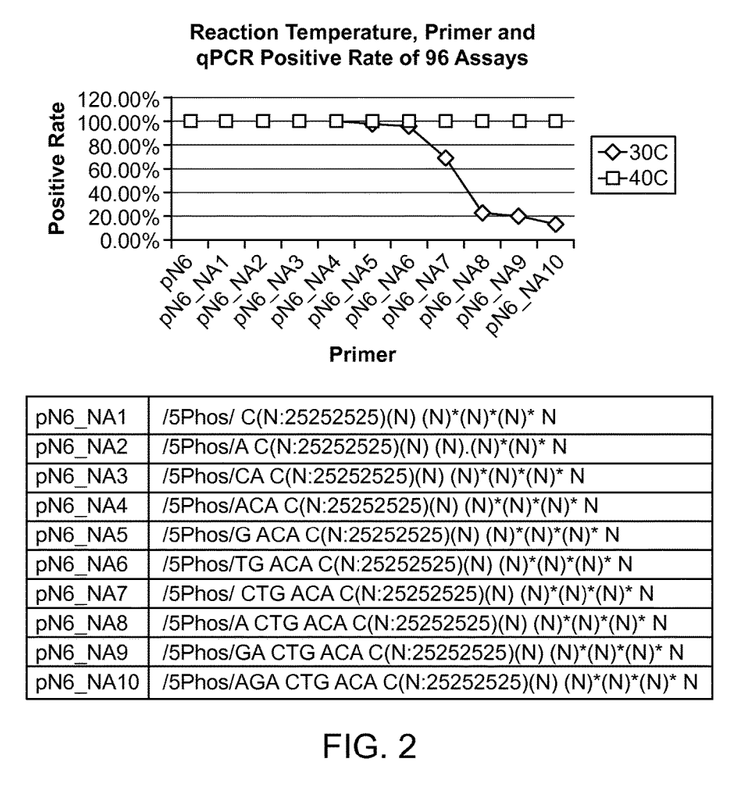
Figure 3:
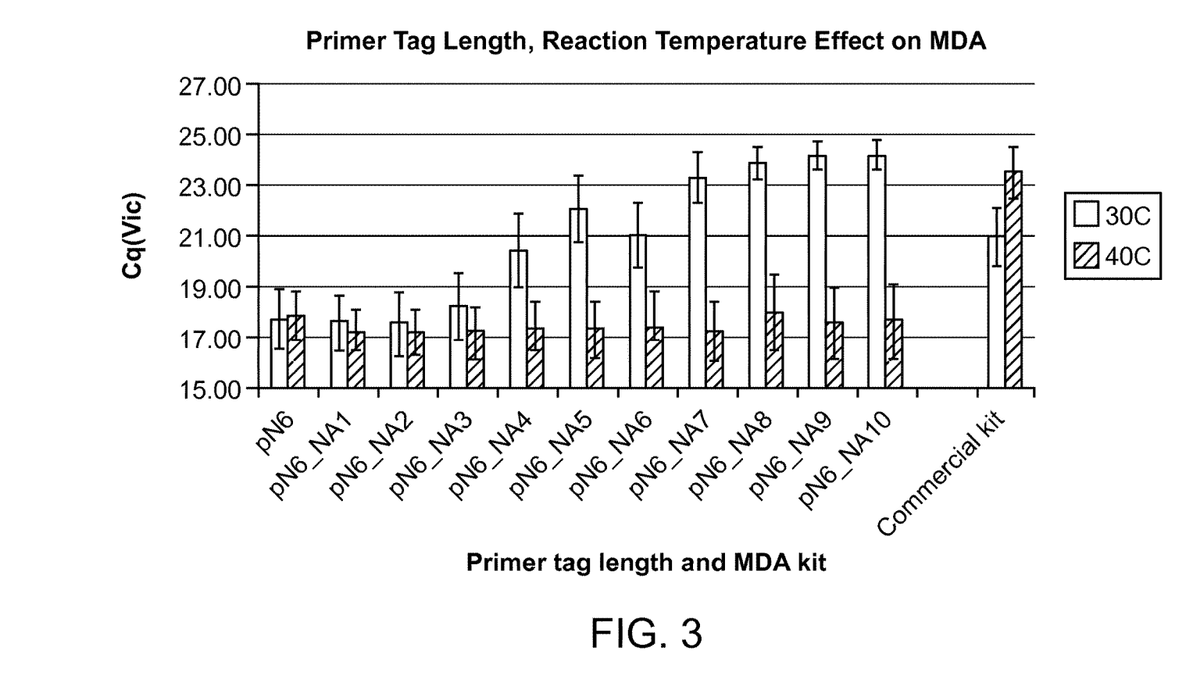
FIG. 3 provides results showing the effects of length of 5' phosphorylated primers and temperature on WGA and yield as measured by qPCR. The WGA reactions were carried out at 30° C. and 40° C. for 3.5 hours as described for FIG. 2. The resulting WGA products were pre-amplified and then quantitated by qPCR on a 96.96 Dynamic Array™ IFC using 96 primers across 22 chromosomes.
Figure 4:
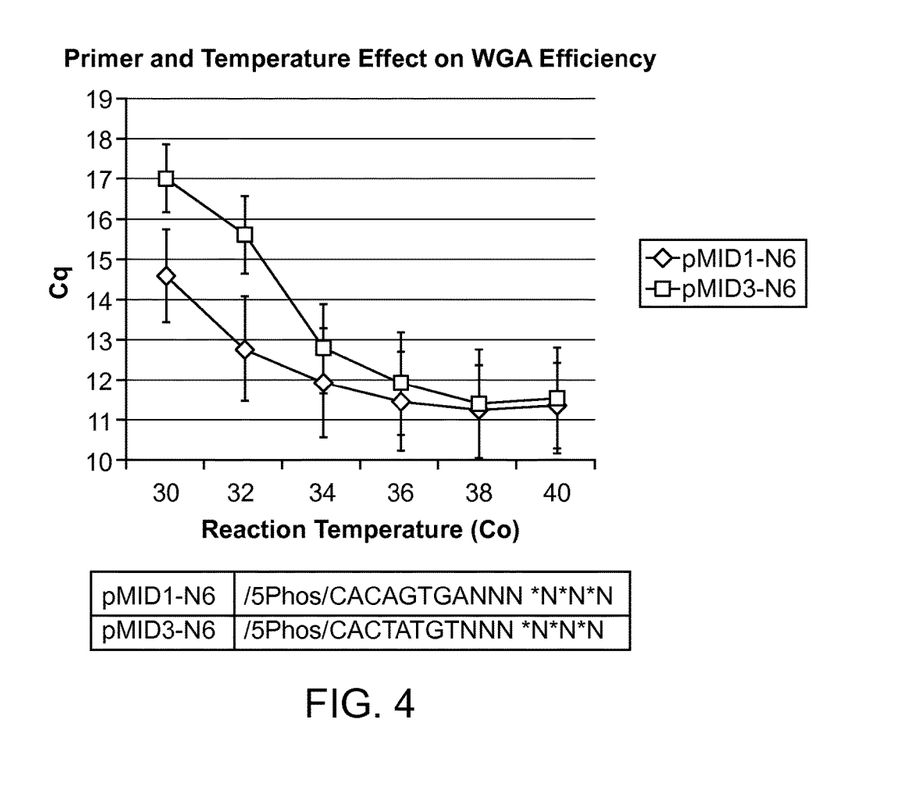
FIG. 4 provides results showing that increased WGA reaction temperature minimized priming differences using random hexamers having the same tag lengths (SEQ ID NOS: 8-9). The reactions were carried out has described for FIG. 2.

Primers having longer "tag" sequences (i.e., the [NA]$_{1-10}$ region) were also evaluated. Higher reaction temperature improved priming efficiency for the primers having the 6-nucleotide random region of the probes with a longer tag as shown in FIGS. 2 and 3, and minimized efficiency differences between different tagged primer designs, FIG. 4.

Figure 1:
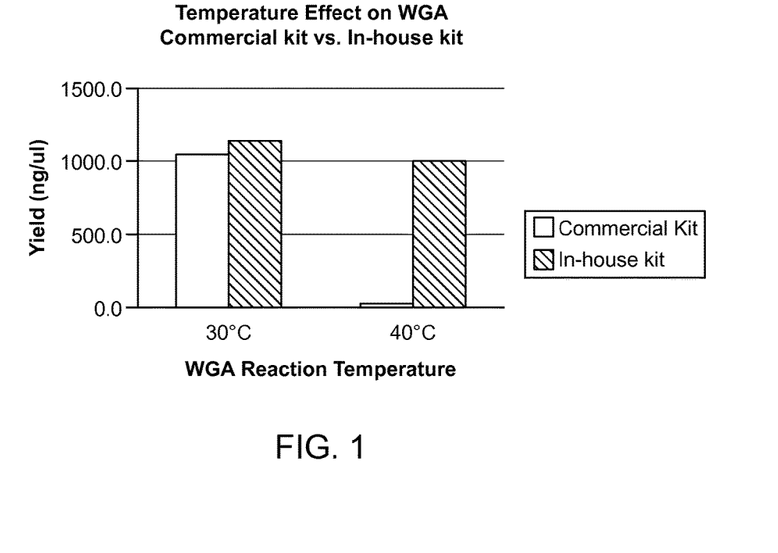
FIG. 1 provides illustrative data showing single-cell WGA results obtained using GenomiPhi™ V2 DNA Amplification kit (GE Healthcare Life Sciences) in comparison to WGA performed using reagents of the invention. The WGA yield was estimated using a picogreen assay (Invitrogen).

The WGA reactions performed at 30° C. showed low yields (FIG. 2) and allelic dropout when the primer tag (NA) length >4, while no impact on both WGA yield and allelic dropout was observed when reacted at 40° C. Furthermore, the reaction performed using the commercial kit generated fewer WGA products at 30° C. and no products at 40° C. (FIG. 1).

In additional assay evaluations, it was also demonstrated that the primer and buffer formulations described in paragraph [0050] provided equivalent WGA results using Phi DNA polymerase from an alternative vendor, New England Biolabs (NEB), (data not shown).

All publications, patents, accession numbers, and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of producing an amplified product, the method comprising:
    (a) preparing a reaction mixture comprising:
        (i) genomic DNA from a single cell;
        (ii) a population of primers comprising from 5' to 3': an NA region, an N region, and an *N region, wherein the primers have the sequence $NA_{1-10}N_{3-5}(*N)_{1-3}$, wherein $NA_{1-10}$ is a defined sequence of from 1-10 nucleotides in length, $N_{3-5}$ is a region of 3-5 nucleotides in length at which random nucleotides are incorporated at each position, and $(*N)_{1-3}$ is a region from 1 to 3 nucleotides in length wherein the nucleotide at each position of $(*N)_{1-3}$ is a thiolated random nucleotide that provides a phosphorothioate linkage; and wherein said defined sequence (iia) is phosphorylated at the 5' end and (iib) consists of an equal balance of purine and pyrimidine bases such that the number of purine nucleotides differs from the number of pyrimidine nucleotide by no more than 1 nucleotide;
        (iii) a Phi29 DNA polymerase;
        (iv) a buffering agent to provide a pH of from 7.2 to 7.7;
    (b) incubating the reaction mixture at a temperature in the range from about 35° C. to about 40° C. for a time sufficient to produce an amplified product.

2. The method of claim 1, wherein the buffering agent is Tris-HCl at a concentration of about 5 mM to about 50 mM.

3. The method of claim 2, wherein the Tris-HCl is at a concentration of about 10 mM to about 30 mM.

4. The method of claim 1, wherein the defined region comprises alternating purines and pyrimidines.

5. The method of claim 1, wherein $NA_{1-10}$ is 7 to 10 nucleotides in length.

6. The method of claim 1, wherein the 3' nucleotide of $NA_{1-10}$ is G or C.

7. The method of claim 1, wherein $N_{3-5}$ is three nucleotides in length and $(*N)_{1-3}$ is three nucleotides in length.

8. The method of claim 1, wherein $NA_{1-10}$ has a 3' nucleotide that is G or C; $N_{3-5}$ is three nucleotides in length; and $(*N)_{1-3}$ is three nucleotides in length.

9. The method of claim 1, wherein the temperature is in the range from about 37° C. to about 40° C.

10. The method of claim 1, wherein the reaction mixture comprises DTT at a concentration of from 1 to 5 mM.

11. The method of claim 1, wherein the reaction mixture comprises $(NH_4)_2SO_4$ at a concentration of 10 mM.

12. A reaction mixture for amplification of genomic DNA from a single cell comprising: (i) genomic DNA from a single cell, (ii) a population of primers comprising from 5' to 3': an NA region, an N region, and an *N region, wherein the primers have the sequence $NA_{A1-10}$ $N_{3-5}$ $(*N)_{1-3}$, wherein $NA_{1-10}$ is a defined sequence of from 1- 10 nucleotides in length, $N_{3-5}$ is a region of 3-5 nucleotides in length at which random nucleotides are incorporated at each position, and $(*N)_{1-3}$ is a region from 1 to 3 nucleotides in length wherein the nucleotide at each position is a thiolated random nucleotide that provides a phosphorothioate linkage; and wherein said defined sequence (iia) is phosphorylated at the 5' end and (iib) consists of an equal balance of purine and pyrimidine bases such that the number of purine nucleotides different from the number of pyrimidine nucleotide by no more than 1 nucleotide (iii) a Phi29 DNA polymerase; and (iv) a buffering agent to provide a pH of from 7.2 to 7.7.

13. The reaction mixture of claim 12, wherein the buffering agent is Tris-HCl at a concentration of about 5 mM to about 50 mM.

14. The reaction mixture of claim 13, wherein the Tris-HCl is at a concentration of about 10 mM to about 30 mM.

15. The reaction mixture of claim 12, wherein the defined region comprises alternating purines and pyrimidines.

16. The reaction mixture of claim 15, wherein $NA_{1-10}$ is 7 to 10 nucleotides in length.

17. The reaction mixture of claim 12, wherein the 3' nucleotide of $NA_{1-10}$ is G or C.

18. The reaction mixture of claim 12, wherein $N_{3-5}$ is three nucleotides in length and $(*N)_{1-3}$ is three nucleotides in length.

19. The reaction mixture of claim 12, wherein $NA_{1-10}$ has a 3' nucleotide that is G or C; $N_{3-5}$ is three nucleotides in length; and $(*N)_{1-3}$ is three nucleotides in length.

20. The reaction mixture of claim 12, further comprising DTT at a concentration of from 1 to 5 mM.

21. The reaction mixture of claim 12, further comprising $(NH_4)_2SO_4$ at a concentration of 10 mM.

* * * * *

SEQUENCE LISTING

```
<160> NUMBER OF SEQ ID NOS: 9

<210> SEQ ID NO 1
<211> LENGTH: 10
<212> TYPE: DNA
<213> ORGANISM: Artificial Sequence
<220> FEATURE:
<223> OTHER INFORMATION: synthetic primer
```

```
<220> FEATURE:
<221> NAME/KEY: misc_feature
<222> LOCATION: (1)..(1)
<223> OTHER INFORMATION: 5' phosphorylated
<220> FEATURE:
<221> NAME/KEY: misc_feature
<222> LOCATION: (5)..(10)
<223> OTHER INFORMATION: N is A, C, T or G
<220> FEATURE:
<221> NAME/KEY: misc_feature
<222> LOCATION: (8)..(10)
<223> OTHER INFORMATION: thiolated nucleotide

<400> SEQUENCE: 1 acacnnnnnn                                                                        10

<210> SEQ ID NO 2
<211> LENGTH: 11
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (1)..(1)
<223> OTHER INFORMATION: 5' phosphorylated
<220> FEATURE:
<221> NAME/KEY: misc_feature
<222> LOCATION: (6)..(11)
<223> OTHER INFORMATION: N is A, C, T or G
<220> FEATURE:
<221> NAME/KEY: misc_feature
<222> LOCATION: (9)..(11)
<223> OTHER INFORMATION: thiolated nucleotide

<400> SEQUENCE: 2
gacacnnnnn n                                                                      11

<210> SEQ ID NO 3
<211> LENGTH: 12
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (1)..(1)
<223> OTHER INFORMATION: 5' phosphorylated
<220> FEATURE:
<221> NAME/KEY: misc_feature
<222> LOCATION: (7)..(12)
<223> OTHER INFORMATION: N is A, C, T or G
<220> FEATURE:
<221> NAME/KEY: misc_feature
<222> LOCATION: (10)..(12)
<223> OTHER INFORMATION: thiolated nucleotide

<400> SEQUENCE: 3
tgacacnnnn nn                                                                     12

<210> SEQ ID NO 4
<211> LENGTH: 13
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (1)..(1)
<223> OTHER INFORMATION: 5' phosphorylated
<220> FEATURE:
<221> NAME/KEY: misc_feature
<222> LOCATION: (8)..(13)
```

```
<223> OTHER INFORMATION: N is A, C, T or G
<220> FEATURE:
<221> NAME/KEY: misc_feature
<222> LOCATION: (11)..(13)
<223> OTHER INFORMATION: thiolated nucleotide

<400> SEQUENCE: 4
ctgacacnnn nnn                                                        13

<210> SEQ ID NO 5
<211> LENGTH: 14
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (1)..(1)
<223> OTHER INFORMATION: 5' phosphorylated
<220> FEATURE:
<221> NAME/KEY: misc_feature
<222> LOCATION: (9)..(14)
<223> OTHER INFORMATION: N is A, C, T or G
<220> FEATURE:
<221> NAME/KEY: misc_feature
<222> LOCATION: (12)..(14)
<223> OTHER INFORMATION: thiolated nucleotide

<400> SEQUENCE: 5
actgacacnn nnnn                                                       14

<210> SEQ ID NO 6
<211> LENGTH: 15
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (1)..(1)
<223> OTHER INFORMATION: 5' phosphorylated
<220> FEATURE:
<221> NAME/KEY: misc_feature
<222> LOCATION: (10)..(15)
<223> OTHER INFORMATION: N is A, C, T or G
<220> FEATURE:
<221> NAME/KEY: misc_feature
<222> LOCATION: (13)..(15)
<223> OTHER INFORMATION: thiolated nucleotide

<400> SEQUENCE: 6
gactgacacn nnnnn                                                      15

<210> SEQ ID NO 7
<211> LENGTH: 16
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (1)..(1)
<223> OTHER INFORMATION: 5' phosphorylated
<220> FEATURE:
<221> NAME/KEY: misc_feature
<222> LOCATION: (11)..(16)
<223> OTHER INFORMATION: N is A, C, T or G
<220> FEATURE:
<221> NAME/KEY: misc_feature
<222> LOCATION: (14)..(16)
<223> OTHER INFORMATION: thiolated nucleotide

<400> SEQUENCE: 7
```
agactgacac nnnnnn                                               16

<210> SEQ ID NO 8
<211> LENGTH: 14
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (1)..(1)
<223> OTHER INFORMATION: 5' phosphorylated
<220> FEATURE:
<221> NAME/KEY: misc_feature
<222> LOCATION: (9)..(14)
<223> OTHER INFORMATION: N is A, C, T or G
<220> FEATURE:
<221> NAME/KEY: misc_feature
<222> LOCATION: (12)..(14)
<223> OTHER INFORMATION: thiolated nucleotide

<400> SEQUENCE: 8
cacagtgann nnnn                                                 14

<210> SEQ ID NO 9
<211> LENGTH: 14
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (1)..(1)
<223> OTHER INFORMATION: 5' phosphorylated
<220> FEATURE:
<221> NAME/KEY: misc_feature
<222> LOCATION: (9)..(14)
<223> OTHER INFORMATION: N is A, C, T or G
<220> FEATURE:
<221> NAME/KEY: misc_feature
<222> LOCATION: (12)..(14)
<223> OTHER INFORMATION: thiolated nucleotide

<400> SEQUENCE: 9
cactatgtnn nnnn                                                 14